United States Patent
Vorm et al.

(10) Patent No.: US 10,564,137 B2
(45) Date of Patent: *Feb. 18, 2020

(54) PRE-ASSEMBLED SEPARATION COLUMNS

(71) Applicant: PROXEON BIOSYSTEMS ApS, Odense C (DK)

(72) Inventors: Ole Vorm, Odense M (DK); Soeren Theodorsen, Odense C (DK); Peter Aagaard Nielsen, Marslev (DK)

(73) Assignee: PROXEON BIOSYSTEMS ApS, Odense C (DK)

(*) Notice: Subject to any disclaimer, the term of this patent is extended or adjusted under 35 U.S.C. 154(b) by 479 days.

This patent is subject to a terminal disclaimer.

(21) Appl. No.: 15/052,353

(22) Filed: Feb. 24, 2016

(65) Prior Publication Data

US 2016/0169846 A1    Jun. 16, 2016

Related U.S. Application Data

(63) Continuation of application No. 12/993,736, filed as application No. PCT/EP2009/055733 on May 12, 2009, now Pat. No. 9,302,415.
(Continued)

(51) Int. Cl.
*B01D 15/22* (2006.01)
*B29C 45/14* (2006.01)
(Continued)

(52) U.S. Cl.
CPC ......... *G01N 30/7266* (2013.01); *B01D 15/22* (2013.01); *B29C 45/14377* (2013.01);
(Continued)

(58) Field of Classification Search
CPC ............... G01N 30/72; G01N 30/7266; G01N 30/6004; G01N 30/6052; G01N 30/6047;
(Continued)

(56) References Cited

U.S. PATENT DOCUMENTS

| 4,211,658 A | 7/1980 | McDonald et al. |
| 5,736,036 A | 4/1998 | Upchurch et al. |

(Continued)

FOREIGN PATENT DOCUMENTS

| DE | 199 05 117 A1 | 8/2000 |
| DE | 299 23 289 U1 | 9/2000 |

(Continued)

OTHER PUBLICATIONS

New Objective, Inc., "PicoTip Nanospray Emitters". Oct. 5, 2009.*
(Continued)

*Primary Examiner* — Benjamin L Lebron
(74) *Attorney, Agent, or Firm* — David A. Schell; Merchant & Gould P.C.

(57) ABSTRACT

There is provided an integrated system for liquid separation, such as LC, CE, affinity chromatography, and ion exchange chromatography, comprising a column and end-fittings embedded in a plastic material, such as a thermoplastic polymer. The system may further comprise an electrospray emitter directly connected with the outlet of the column, wherein a substantial part of the emitter is covered with the polymer material. There is also provided a method by which a separation column along with the accompanying end fittings for connection with adjacent liquid conduits is embedded in a polymer matrix. This configuration e.g. ensures that the factory-made, correct attachment of the fittings to the column is preserved (since the matrix prevents further user intervention, accidental or otherwise). Accordingly, the responsibility for the correct attachment of the fittings is shifted from the end user to the manufacturer.

13 Claims, 4 Drawing Sheets

Related U.S. Application Data

(60) Provisional application No. 61/055,224, filed on May 22, 2008.

(51) Int. Cl.
  *G01N 30/60* (2006.01)
  *G01N 30/72* (2006.01)

(52) U.S. Cl.
  CPC ... *B29C 45/14426* (2013.01); *G01N 30/6004* (2013.01); *G01N 30/6052* (2013.01); *G01N 30/6047* (2013.01); *G01N 30/6091* (2013.01)

(58) Field of Classification Search
  CPC ............ G01N 30/6091; B01D 15/22; B29C 45/14377; B29C 45/14426
  See application file for complete search history.

(56) References Cited

U.S. PATENT DOCUMENTS

| | | | |
|---|---|---|---|
| 5,747,799 A * | 5/1998 | Franzen | H01J 49/0422 |
| | | | 250/282 |
| 5,782,964 A * | 7/1998 | Mustacich | G01N 30/30 |
| | | | 73/23.25 |
| 5,788,166 A * | 8/1998 | Valaskovic | B05B 5/0255 |
| | | | 239/690 |
| 5,863,401 A * | 1/1999 | Chen | G01N 27/44726 |
| | | | 204/451 |
| 5,938,919 A * | 8/1999 | Najafabadi | G01N 30/6047 |
| | | | 210/198.2 |
| 5,993,633 A | 11/1999 | Smith et al. | |
| 6,139,734 A | 10/2000 | Settlage et al. | |
| 6,727,497 B2 * | 4/2004 | Scalf | H01J 49/165 |
| | | | 250/282 |
| 6,736,973 B1 | 5/2004 | Podgornik et al. | |
| 7,101,477 B1 | 9/2006 | Willis et al. | |
| 7,858,932 B2 | 12/2010 | Finch et al. | |
| 2002/0032408 A1 | 3/2002 | Parker et al. | |
| 2005/0077222 A1 | 4/2005 | Dawes et al. | |
| 2006/0022131 A1 * | 2/2006 | Tojo | G01N 30/7266 |
| | | | 250/288 |
| 2006/0027490 A1 | 2/2006 | DeMarco | |
| 2006/0060515 A1 | 3/2006 | Benevides et al. | |
| 2007/0068872 A1 | 3/2007 | Gerhardt et al. | |
| 2008/0038152 A1 | 2/2008 | Van Pelt | |
| 2010/0025331 A1 | 2/2010 | Cabrera Perez et al. | |
| 2010/0193683 A1 | 8/2010 | Marto | |
| 2011/0042566 A1 | 2/2011 | Dubey et al. | |
| 2011/0278214 A1 | 11/2011 | Benevides et al. | |

FOREIGN PATENT DOCUMENTS

| | | | |
|---|---|---|---|
| DE | 10 2007 008 360 A1 | 8/2008 | |
| EP | 0 884 081 A2 | 12/1998 | |
| EP | 1 676 618 A1 | 7/2006 | |
| JP | 2007-64725 | 3/2007 | |
| WO | WO 2005/072164 A2 | 8/2005 | |
| WO | WO 2007/009493 A1 | 1/2007 | |
| WO | WO-2007009493 A1 * | 1/2007 | ............ B29C 43/18 |
| WO | WO 2007/041315 A2 | 4/2007 | |
| WO | WO 2008/112702 A1 | 9/2008 | |

OTHER PUBLICATIONS

Top Seiko Co., Ltd., "Fused silica glass (fused quartz) & borosilicate glass—custom machined parts". Accessed May 31, 2018. https://top-seiko.com/works/material-cat/quartz_glass/.*

* cited by examiner

PRE-ASSEMBLED SEPARATION COLUMNS

This application is a Continuation Application of U.S. patent application Ser. No. 12/993,736, filed Feb. 2, 2011, which is a National Stage Application of PCT/EP2009/055733, filed May 12, 2009, which claims benefit of Serial No. 61/055,224, filed May 22, 2008 in the United States and which applications are incorporated herein by reference. To the extent appropriate, a claim of priority is made to each of the above disclosed applications.

BACKGROUND OF THE INVENTION

Proteomics, being the study of protein structure and function, is a research focus for decades to come as it can allow one to elucidate the fundamentals of life and the molecular basis of health and disease. Analysis of complex protein mixtures usually involves two steps: molecular separation and identification/characterization. The method of choice for protein identification and characterization is mass spectrometry (MS) where the analytes of interest are ionized by electrospray ionization (ESI) or matrix-assisted laser desorption/ionization (MALDI). Two separation methods are dominating in the field of proteomics: 2-dimensional gel-electrophoresis (2D-GE) and high-performance liquid chromatography (HPLC). An important advantage of HPLC compared to 2D-GE is its relatively simple coupling to MS through ESI.

One of the demands of the fast growing proteomic research area is a miniaturization of bioanalytical techniques, see e.g. T. Laurell and G. Marko-Varga, "Miniaturization is mandatory unraveling the human proteome", Proteomics, (2002), Vol. 2, pp. 345-351, Lion, N.; Rohner, T. C.; Dayon, L.; Arnaud, I. L.; Damoc, E.; Yonhnovski, N.; Wu, Z. Y.; Roussel, C.; Josserand, J.; Jensen, H.; Rossier, J. S.; Przybylski, M.; Girault, H. H. Electrophoresis 2003, 24, 3533-3562. The miniaturization in liquid chromatography is evidenced by the increasing use of smaller beads, smaller diameter columns, and correspondingly smaller flow rates. Under laboratory conditions miniaturization has led to higher resolution, increased sensitivity, and faster separation.

Another of the demands is the elimination of user intervention with the bioanalytical techniques in order to ensure reproducible results. In this respect, a commercially available microfluidic chip manufactured by Agilent Technologies, Inc. integrates a trapping column, a separation column and an electrospray source (i.e. the emitter) within a single structure, see e.g. Gottschlich, N.; Jacobson, S. C.; Culbertson, C. T.; Ramsey, J. M. Anal Chem 2001, 73, 2669-2674; Fortier, M. H.; Bonneil, E.; Goodley, P.; Thibault, P. Anal Chem 2005, 77, 1631-1640. Meanwhile this system is based on microfluidic chip technology, which is still not a fully matured technology. And whereas this technology provides many user friendly simplifications, the chromatographic performance is currently not able to match that of non-chip based systems. DE 299 23 289 U1 discloses a method for providing an integrated separation column including end fittings embedded in plastic material. Prior to embedding the column in a plastic material the method involves wrapping a heat contracting tube around the column before plastifying and molding a part based on a plastic material within a forming tool for shaping a desired form around the separation column and end fittings.

While conventional HPLC columns (i.e. columns with fittings for connecting to conventional instruments) for use with nano-liter flow rates (also referred to as nano-LC) show superior performance relative to chip-based LC, the problem with incorrect assembly of fittings and fluid connections often compromises the advantages associated with conventional nano-LC columns. In other words, incorrect connections of LC transfer tubing to the LC columns may result in leaks and consequently poor sensitivity and chromatographic separation. Also, incorrect connection of a conventional nano-electrospray emitter after the LC column may give rise to undesired dead-volumes which also leads to reduced sensitivity and poor separating power.

Thus, the integration of a complete LC-ESI system, wherein conventional LC columns and spray emitters are used, and wherein the end-user should not establish the correct fluid connections (correct assembling of fittings), is highly desirable.

The columns and transfer lines ordinarily used in liquid chromatography systems that employ flow rates less than 10 µL/minute most frequently have very narrow inner diameters as well as outer diameters. Consequently, such transfer lines and columns may be physically fragile. Thus it is also highly desirable to provide some means of mechanical relief from strain, pressure, bends, twists etc. such that the thin tubing components are protected and become robust enough to withstand use in everyday laboratory work.

The commonly used interface between chromatography and mass spectrometry is made up by the electrospray ion-source. In the ion source, the eluate from the LC column is passed through an emitter that is held at an electric potential that usually differs by one or more kilovolts from an opposing inlet orifice of the mass spectrometer. This enables the eluate, and subsequently the analytes, to adopt electric charges (i.e. become ionized) such that the ionized analytes may be analyzed in the mass spectrometer. The high electric potential differences present a safety hazard if the charged areas can be touched by the operator. Thus it is highly desirable to efficiently shield as many components as possible that are at the elevated potential.

SUMMARY OF THE INVENTION

The present invention provides an integrated system for liquid separation, such as LC, CE, affinity chromatography, and ion exchange chromatography, comprising a column and end-fittings embedded in a plastic material, such as a thermoplastic polymer. The system may further comprise an electrospray emitter directly connected with the outlet of the column, wherein a substantial part of the emitter is covered with the polymer material.

The present invention is thus based on a method by which a separation column along with the accompanying end fittings for connection with adjacent liquid conduits is embedded in a polymer matrix. This configuration e.g. ensures that the factory-made, correct attachment of the fittings to the column is preserved (since the matrix prevents further user intervention, accidental or otherwise). Accordingly, the responsibility for the correct attachment of the fittings is shifted from the end user to the manufacturer.

In accordance therewith the present invention is directed to a method for providing an integrated separation column including end fittings embedded in a plastic material, said method comprising:

introducing a separation column with end fittings into a forming tool, and plastifying and molding a part based on a plastic material within the forming tool for shaping a desired form around the separation column and end fittings.

Plastifying the part may be achieved in various ways, preferably by heating the plastic material beyond the softening temperature for bringing it in its softening range and making it soft. In a preferred embodiment the entire column and fittings are surrounded by the plastic material. The molding part may be a pre-formed part adapted to the shape of the integrated separation column and of the forming tool.

The forming of the molding part may be achieved by closing the forming tool and exerting pressure on the pre-formed part. Alternatively, this is achieved by closing the forming tool and heating the forming tool together with the plastic material.

In preferred embodiments of the present invention the forming of the molded part may be achieved by injecting molten plastic material into a mold wherein the LC column with fittings and other related or required components are located and allowing the molten plastic to embed these parts and cool off and harden to become solid. Alternatively the molded part may be shaped by exerting pressure on the plastic material caused by the thermal expansion of the plastic material by heating the closed forming tool comprising the plastic material, alternatively by exerting pressure on the plastic material by closing the forming tool, or actively cooling down the plastic material and/or the forming tool. Still another alternative embodiment may be achieved by mixing chemicals that subsequently polymerize inside a mold thereby embedding the LC column with fittings and other related components.

The plastic material used in the method of the present invention is at least one of: a thermoplastic material, polyetheretherketone (PEEK), one of a broad range of flouropolymers, in particular perfluoroamines (PFA) or flourinated ethylene-propylene copolymer (FEP), duroplastic material or compound, in particular polyimide, and liquid crystal polymers (LCP).

Preferably, the plastic materials of the present invention are thermoplastic hotmelts based on polyamide, such as those marketed under the tradename MacroMelt (Henkel Kommanditgesellschaft). These includes at least one room-temperature-flowable polymerizable compound in combination with a polymeric matrix present in an amount sufficient to render the composition non-flowable at temperatures of at least about 49° C. The polymerizable compound or composition may be selected from a wide group of materials including anaerobics, epoxies, acrylics, polyurethanes, olefinic compounds and combinations thereof. Anaerobic compositions are most desirable since they have unique applications in many threadlocking and sealant areas where the need for a non-flowable material exists. The polymeric matrix may be selected from polyamides, polyacrylamides, polyimides, polyhydroxyalkylacrylates and combinations thereof. In one desired embodiment of the present invention an anaerobic adhesive composition is provided which includes a polymerizable (meth) acrylate monomer, a polymerization initiator for the monomer, and a polymeric matrix material miscible or otherwise compatible with the monomer. The matrix material is present in an amount sufficient to render the composition non-flowable at temperatures of at least about 210° C. The polymeric matrix and polymerizable component readily form a stable mixture or combination without phase separation of component parts. The method of the present invention thus produces an embedded and integrated separation column. This integrated solution may further comprise an electrospray emitter that isconnected directly or via a transferring conduit with the separation column through one of the end fittings. Preferably the electrospray emitter is made of a section of electrically conductive narrow bore metal tubing that has been shaped at the terminal end (i.e. the location of the formation of the electrospray) either by means of electrochemical etching or mechanical polishing such that it has a very sharp tip. Alternatively the emitter can be based on a glass capillary that optionally can be coated with an electrically conductive material. In a preferred embodiment, the present invention provides an integrated separation column, wherein the integrated separation column and electrospray emitter are embedded in the same plastic material.

In order to meet the most relevant requirements in relation to the operation of the column, the integrated separation column may be equipped with heating/cooling bars and thermo sensor in contact with the column and embedded in the plastic material.

In relation to the electrospray emitter a high voltage (HV) contact in communication with the electrically conductive part of the emitter may be provided in accordance with the present invention; this HV contact is also embedded in the plastic material but penetrates the outer surface of the material for electrical contact with an external power source. Preferably the plastic material is formed such that this electrical contact is made in a manner that eliminates the possibility for the operator to come into contact with the HV source or at least reduces the risk of the event.

For optimum performance, channels for gas flow may also be embedded in the plastic material; the outlet of these channels being in close proximity with the apex of the emitter, whereby gas leaving the outlet assists in the desolvation of the spray cloud.

In order to facilitate identification of the integrated column, the embedded components may further comprise an identification tag, such as a radio frequency identification tag (RFID) embedded in the plastic material.

In order to ensure correct positioning of the integrated column and electrospray emitter relative to e.g. the MS inlet, the present invention also provides a frame adapted for receiving the integrated column.

It is important to emphasize that the present invention is also directed to an integrated separation column comprising end fittings embedded in a plastic material, irrespective of the method used for the embedment in the plastic material. Also, in the this general embodiment the integrated separation column may further comprise an electrospray emitter directly connected with the separation column through one of the end fittings. Moreover, as in the other embodiments of the present invention the plastic material is at least one of: a thermoplastic material, preferably based on polyamide and/or polyurethane, polyetheretherketone (PEEK), one of a broad range of flouropolymers, in particular perfluoroamines (PFA) or flourinated ethylene-propylene copolymer (FEP), duroplastic material or compound, in particular polyimide, liquid crystal polymers (LCP). Finally, the integrated separation column may in agreement with the other described embodiments of the present invention further comprise an RFID-tag, heating/cooling bars and thermo sensor, a high-voltage contact point for the electrospray emitter, counter electrode(s) with a geometry that benefits definition of the field lines around the electrospray emitter, and channels for gas flow embedded in the plastic material.

Coupling with a laboratory apparatus, for example a mass spectrometer becomes easier. Additionally an exact and repeatable positioning process of the integrated column relatively to the frame can be guaranteed by molding the plastic material to a shape that provides a tight fit in a receiving adapter on the laboratory apparatus. The ease and accuracy of the positioning may be further enhanced by use of shapes that by design help lock the two items into a given position (e.g. by way of convex/concave mating surfaces, magnets or spring loads). This also enables the exact positioning of the integrated column into a laboratory apparatus if the frame is positioned precisely in the laboratory apparatus.

In addition to shielding the column, emitter and fittings from disassembly (whether intentional or accidental), the plastic embedding also renders physical strength to some otherwise rather fragile components that are prone to be damaged through everyday usage in laboratory environments. Nano-LC columns are frequently and advantageously made from a piece of silica glass tubing where said tubing typically is 100 mm long but has an outer diameter of around 300 µm and hence the tubing can easily break. Typically such silica glass tubing has an outer polymer lining of a few micrometers thickness that renders some strength but the glass tubing is still easily broken. Similarly the emitter is made from a very narrow piece of metal or glass tubing and can readily be damaged by contact with other items. The plastic embedding described herein makes the integrated column robust and durable such that they cannot readily break by accident. The protection of the column and emitter includes protection from physical strains, twists, bends as well as the pressure of the liquid inside the tubing whose thin walls are made several fold thicker by the plastic matrix being in direct (chemical) contact with the outer surface of the tubing.

The chromatographic retention times that are observed for the individual analytes are highly dependent on the temperature at which the separation takes place. Slight variation in temperature can lead to pronounced shifts in retention times and in order to obtain reproducible data, it is often sought to maintain stable ambient temperatures for the column. NanoLC columns—by virtue of their small diameters—can readily exchange heat with the surrounding air. This is however prevented by the plastic matrix which provides thermal insulation of the columns and therefore assists in maintaining stable column temperatures.

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

DETAILED DESCRIPTION OF THE INVENTION

Figure 1:
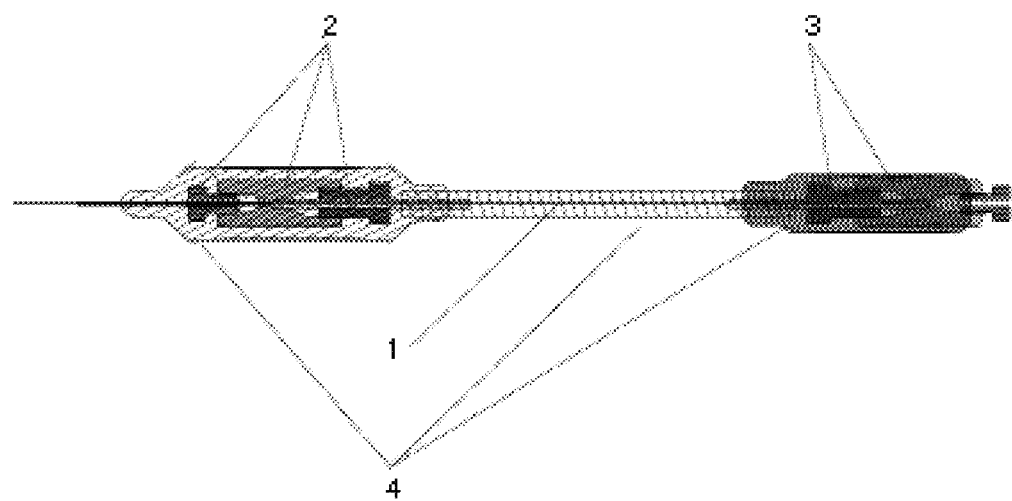
FIG. 1 shows an arrangement with an HPLC column being part of the arrangement with two conduits and fittings. One conduit is the electrospray emitter and the other conduit is the column body.
Figure 2:
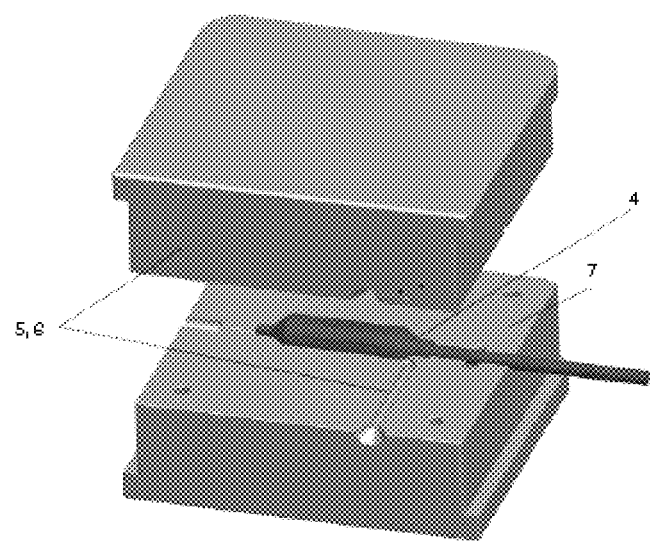
FIG. 2 shows a view of the arrangement of FIG. 1, but with the forming tool (in two halves) encompassing the arrangement with a surrounding molding part.

The arrangement as shown in FIGS. 1 and 2 comprises a pre-assembled HPLC column (1) with fittings (2, 3). The molding part (4) comprises a plastic material, for example, a thermoplastic material, for example, polyamide and polyurethane based MacroMelt™. The plastic material is adapted for being formed with a forming tool (5) comprising a mold (6). The mold (6) comprises an inner surface (7). FIG. 2 shows a view of the arrangement of FIG. 1, but with the closed forming tool (5). In some embodiments, the plastic material can be melted completely and afterwards cooled down to ambient temperature. Therefore, the plastic material can realize a chemical bond with the outer surfaces of the column and fittings.

Figure 3:
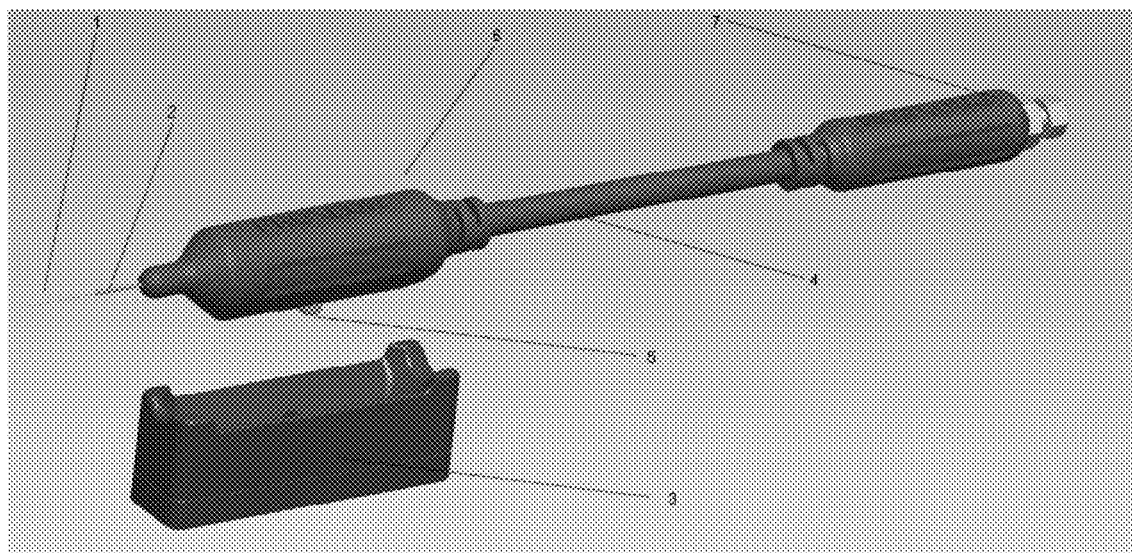
FIG. 3 shows a three-dimensional view of the arrangement of FIG. 2 completely fabricated and without the forming tool. Also shown is the frame (or adapter) that fits to the outer shape of the now embedded column and fitting. The pin for the HV connection can be seen underneath the fitting that connects the electrospray emitter and the column body.

FIG. 3 shows a three-dimensional view of the arrangement of FIG. 2 completely fabricated and without the forming tool. Also shown is the frame (or adapter) that fits to the outer shape of the now embedded column and fitting. The pin for the HV connection can be seen underneath the fitting that connects the electrospray emitter and the column body. Specifically there is shown an emitter 1, a sleeve 2 that fits the emitter, a cradle 3 that is mounted on electrospray source and provides means of snap-on fitting of embedded column via magnets, a chromatography column 4 embedded in plastic, a high voltage connector pin 5, an embedded union 6 that connects column and emitter, a partly embedded union 7 that connects column and transfer line from chromatography system.

Figure 4:
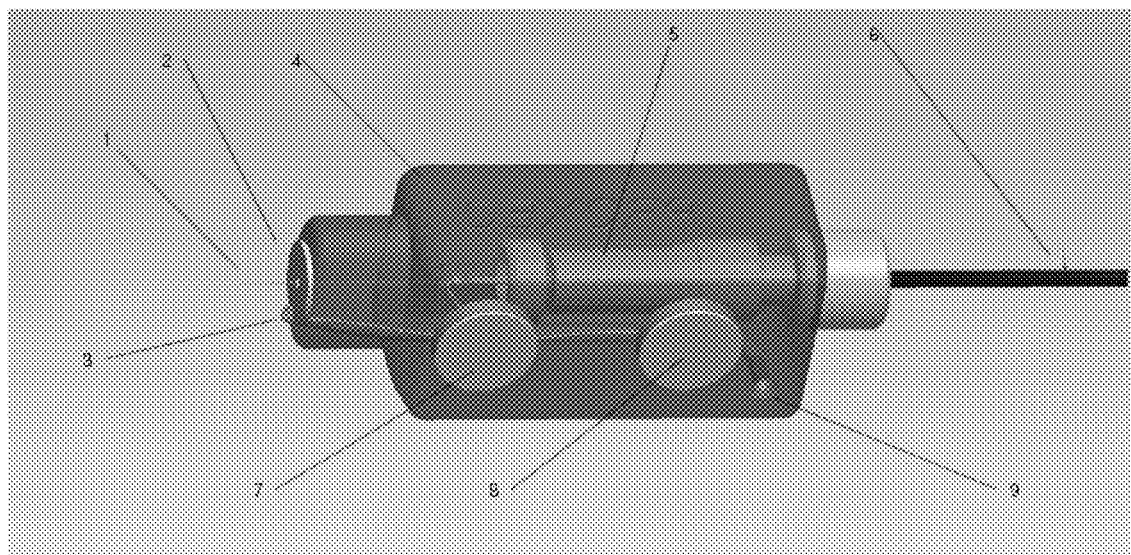
FIG. 4 shows a three dimensional view of an alternative arrangement where an integrated emitter and column is embedded along with magnets to provide a snap-on connection to a frame, as well as a gas flow line that points towards the emitter tip such that it can pneumatically assist the desolvation of the sprayed droplets, and also shown is an annular counter electrode that can be used to optimize the electric field lines between the emitter and the inlet orifice.

FIG. 4 shows a three dimensional view of an alternative arrangement where an integrated emitter and column is embedded along with magnets to provide a snap-on connection to a frame, as well as a gas flow line that points towards the emitter tip such that it can pneumatically assist the desolvation of the sprayed droplets, and also shown is an annular counter electrode that can be used to optimize the electric field lines between the emitter and the inlet orifice. Specifically there is shown an emitter 1, a counter electrode 2, such as an annular disc that assists in controlling the electrical field lines between the column/emitter arrangement and the inlet orifice of the mass spectrometer, an exit opening 3 of the gas conduit (a stream of air or inert gas, e.g. nitrogen, may be used to facilitate desolvation of the electrosprayed droplet), a plastic matrix cast 4 around the union that connects emitter and column, a union 5 that connects emitter and column (made from metal or polymer material), a column tube 6 (not embedded in the present drawing, made from polymer, metal, or glass tubing), a magnet 7 (with dual purpose: i) enables snap-on fitting to adapter frame; and ii) connects high voltage to the electrospray emitter), a magnet 8 (with dual purpose: i) enables snap-on fitting to adapter frame; and ii) connects high voltage to the counter electrode), and finally an entrance opening 9 of the gas conduit.

According to the present invention, devices and techniques for HPLC applications are provided. More particularly, the invention provides a method and system for performing separation of compounds. Merely by way of example, the invention has been applied to a high pressure liquid chromatography process. But it would be recognized that the invention has a much broader range of applicability.

Embodiments may comprise one or more of the following: a part surrounding an HPLC column with end fittings that are plastified and molded within a forming tool for forming or for shaping the form of the integrated column and for fixing the fittings (nuts and bolts). The molding part comprises a plastic material. Advantageously, this technique enables sealing and positioning of said fittings and column. Advantageously, the forming tool can form the shape, for example the outer shape, of the integrated column to a desired shape with a good dimensional stability and a high reproducibility. Additionally, close tolerances can be held or maintained, for example, by exactly adjusting the process parameters like the temperature and the detention time within the forming tool.

The molding part can be realized as a pre-formed part, wherein the shape of the pre-formed part is adapted to the shape of the column and fittings and of the forming tool. The pre-formed molding part can be plastified by heating the plastic material above or beyond the softening temperature and bringing it in its softening range for making it soft and pliable. Advantageously, the plastified plastic material can be evenly formed to the outer surfaces of the column and fittings. This enables a homogenous force distribution across the surfaces. Besides this, the mechanical stress after forming can be reduced.

In embodiments, the pre-formed molding part can comprise two or more component parts, wherein said component parts are joined to each other.

Most advantageously, the molding part can be realized by injecting molten plastic material into a mold and allowing this to cool to such temperature where the plastic forms a stable solid which may be flexible or entirely rigid depending on the chosen chemical composition of the plastic material.

In embodiments, the forming tool is equipped at least partly with at least one HPLC column and fittings and with at least one pre-formed part. The pre-formed part comprises the plastic material and is adapted to be formed for producing the sheath around the column and fittings. Advantageously, the pre-formed part can be easily produced with a relative low exactness, for example, by extruding, injection molding, or alike and is thus cost effective.

Advantageously, the formed columns fulfill a given set of tolerances. The dimensional consistency is guaranteed by forming the pre-formed molding part or the molten plastic by the forming tool. One forming tool can be used for different insets, different types of conduits, for example, polymer tubing, capillaries, glass capillaries, fused silica capillaries, rods, bars, needles, syringes or alike.

Before forming the molding part around the column and fittings, an outer surface of the column and fittings can be at least partly surrounded with the pre-formed molding part. After forming, the functional element can adhere to the outer surface of the conduit, for example, by frictional forces, shrink forces and/or a chemical bond. For forming the molding part around the column and fittings, the forming tool can be closed for exerting pressure on the softened pre-formed part, or, as the case may be, allow a molten plastic to be injected under pressure.

The tool can be closed and heated together with the plastic material of the pre-formed part. Possibly, pressure can be exerted on the plastic material by thermal expanding the plastic material by heating it within the closed forming tool. Besides this, the pressure can be exerted by a moving piston of the forming tool. After forming, the forming tool can be opened. Possibly, the tool can be opened before cooling down the already formed molding part. By this, the production quantity per time unit can be increased. The step of cooling down the functional element to ambient temperature can be parallelized with the step of forming the next unit. Or, for adjusting, for example, a lower and/or exacter temperature gradient, the plastic material can be cooled down within the forming tool. The cooling step can also be forced actively by well known practices like air cooling, or fluidic cooling of the parts, or surrounding parts, or with a thermocouple.

Advantageously, the plastic material can be shrunk on the outer surface of the column and fittings by cooling the plastic material down to ambient temperature.

Embodiments may comprise one or more of the following. The plastic material can be heated within the forming tool close to or above the melting temperature for bringing the plastic material to the softening range or for melting the plastic material. By this, a chemical bond between the outer surface and the plastic material is possible. For avoiding a similar chemical bond of the plastic material at the boundary point of the inner surface of the mold to the forming tool, one can choose a tooling material which will not cling together with the plastic material or the mold and/or the forming tool can be coated with an according release agent.

The plastic material can be a thermoplastic material or compound, for example polyamide and polyurethane, polyetheretherketone (PEEK), flouropolymers for example perfluoroamines (PFA) or flourinated ethylene-propylene copolymer (FEP), duroplastic material or compound for example polyimide, LCP (liquid crystal polymers), and/or perfluoroamines (PFA), comprising advantageous material properties; for example, high persistence against aggressive solvents and good properties for sealing.

Preferably the plastic material comprises molding compounds are thermoplastic hotmelts based on polyamide. The products of the Macromelt® series are exciting not only technically but also ecologically as they are produced from renewable raw materials. No chemical reactions take place during application and no solvents are released. Macromelt® hotmelts are processed at temperatures of 130 to 240° C. and can be used at temperatures from −40 to +140° C. Adhesion to PA, PBT, PVC and similar polar substrates is very good. Macromelt® hotmelts may be distinguished from other hotmelts by their exceptional mechanical properties. With a high Shore hardness, it produces a plastic-like surface, which is achieved by its high crystalline shares. Macromelt® hotmelts have extremely good mechanical and chemical strength and an excellent adhesion to the materials used to manufacture separation columns, including PEEK, metal, and PVC.

Additionally, the plastic material can be coated after forming with a sealing material, for example, with silicone, rubber, Teflon®, epoxy, or alike.

Further embodiments of the present invention relate to an arrangement of a coupling for bringing conduits in communication. The coupling comprises at least one conduit adapted for conducting a medium, for example, an HPLC column, and an element, such as a fitting with ferules, adapted for bringing the conduit in communication with another conduit, for example, an electrospray needle.

In an alternative embodiment of the present invention only the fittings and/or minor parts of the conduits are embedded in the molding material in order to prevent the disassembly of the arrangement and shield from the electric HV potential, whereas; in this embodiment the actual conduits, which may be the column body or a transfer line, may be so long as to be impractical or impossible to include in the embedded volume in their entirety.

Column Dimensions

The chromatography columns of the present invention may have a variety of sizes depending on the use of the chromatography column. For example, chromatography columns of the present invention may have any height (also referred to herein as the column length), although columns almost invariably have an overall height of less than 3 meters (m) and usually less than 1 meter and typically a height around 10 cm. In some embodiments, chromatography columns of the present invention have a height (or length) ranging from about 0.50 mm to about 1.0 m.

Chromatography columns of the present invention may also have a tubular wall structure of an overall thickness that varies, depending on the requirements of the column (e.g., the pressure capacity). Typically, chromatography columns of the present invention have a tubular wall structure overall thickness of up to about 50 mm. In some embodiments, chromatography columns of the present invention have a tubular wall structure overall thickness ranging from about 25 μm to about 10 mm.

Chromatography columns of the present invention may be constructed from the above-referenced materials in order to withstand an internal pressure that varies depending on the end use of a given column. Typically, chromatography columns of the present invention are constructed to have a pressure capacity of up to about 50,000 psig. In some embodiments, chromatography columns of the present invention are constructed to have a pressure capacity ranging from about 500 to about 50,000 psig.

Fittings

Fittings as used for the present invention may be constructed from a wide range of polymer materials where often a hard and chemically inert polymer such as PEEK is preferred. Alternatively fittings may be made of a range of metals where stainless steel and titanium usually are the preferred materials. For the purpose of making electrical contact between an electrospray emitter and the power supply that supplies the electrospray potential as described herein, it is advantageous that the fitting materials be conductive, which means metal is usually the material of choice.

Fittings include ferrules or gaskets that provide a seal between the body of fitting and the conduits that are to be connected. The build-up of dead-volumes or un-swept volumes inside the conduits and fittings is best avoided by butt-connecting all conduits, which leads to the best chromatographic performance. Despite the foregoing, conduits that are joined inside the fittings, may still be kept apart by small distances made up by the thickness of filter-disks, metal grids, or similar without noticeable deterioration of the chromatographic resolving power of the integrated unit.

Electrospray Emitter

The electrospray emitters as used for the present invention may be made of glass tubing which may end in a sharp or a blunt tip. It is usually preferable to have a sharp and tapered tip such as that obtained when using an automated capillary puller (e.g. from Sutter Instrument, Inc., Novato, Calif., USA) since such emitters provide a more stable spray than blunt emitters do. Typically such tapered emitters have an outer diameter of about 360 μm and an inner diameter of 5 μm to 100 μm whereas the orifice at the tapered tip is usually around 1 μm to 15 μm. The length of such emitters is usually between 30 mm and 60 mm but may also be longer or shorter.

Still better performance is usually obtained from emitters that are made of a conductive material, hereunder steel, and bi-modal materials such as gold and nickel. Some embodiments of the present invention preferable use stainless steel emitters than have an outer diameter between 100 μm and 500 μm and an inner diameter between 5 μm and 100 μm.

EXAMPLE 1

Preparation of a Chromatography Column Embedded in a Thermoplastic Polymer

An integrated HPLC column with electrospray needle having the structure shown in FIG. 3 was manufactured by following injection molding steps as previously described. The specifications are given below.

Outer diameter of column: 360 μm
Inner diameter of column: 75 μm
Length of column: 10 cm
Material of column tubing: Polyimide coated fused silica glass
Packing material of column (stationary phase): ReprosilPur C18, 3 μm beads, 120 nm pores
Outer diameter of emitter: 150 μm
Inner diameter of emitter: 20 μm
Length of emitter: 4 cm
Material of emitter: Stainless steel, electropolished tip
Embedding material: polyamide or polyurethane based MacroMelt™
Process: Injection molding, using a Moldman handset
Forming temperature: about 180° C. to 240° C.
Forming time: around 30 sec.
Cooling temperature: to ambient
Cooling time: as required
Molds: aluminium, manufactured in-house
Molding process done in 3 or 4 steps in sequence.

The invention claimed is:

1. An integrated separation column comprising end fittings, a separation column, and an electrospray emitter, wherein the separation column is connected directly or via a transferring conduit with the electrospray emitter through one of the end fittings, and wherein the separation column, the end fittings, and the electrospray emitter are embedded in a plastic material that forms a housing that holds the separation column, the end fittings, and the electrospray emitter in place, the plastic material covering a substantial part of the electrospray emitter and extending continuously to cover the one of the end fittings, the separation column, and a substantial part of an additional one of the end fittings, the plastic material further enclosing channels for gas flow.

2. The integrated separation column of claim 1, wherein the electrospray emitter is based on a glass capillary coated with an electrically conductive material.

3. The integrated separation column of claim 1, wherein the plastic material is at least one of: a thermoplastic material, polyetheretherketone (PEEK), fluoropolymer or duroplastic material or compound.

4. The integrated separation column of claim 3, wherein the plastic material is the thermoplastic material, and the thermoplastic material comprises polyamide and/or polyurethane.

5. The integrated separation column of claim 3, wherein the plastic material is the fluoropolymer, and the fluoropolymer comprises perfluoroamines (PFA) or fluorinated ethylene-propylene copolymer (FEP).

6. The integrated separation column of claim 3, wherein the plastic material is the duroplastic material or compound, and the duroplastic material or compound comprises polyimide or liquid crystal polymers (LCP).

7. The integrated separation column of claim 1 further comprising an RFID-tag.

8. The integrated separation column of claim 2, wherein the electrically conductive material is a conductive metal.

9. The integrated separation column of claim 8, wherein the conductive metal is stainless steel.

10. An integrated separation column comprising end fittings, a separation column, and an electrospray emitter, wherein the separation column is connected directly or via a transferring conduit with the electrospray emitter through one of the end fittings, and wherein the separation column, the end fittings, and the electrospray emitter are embedded in a plastic material that forms a housing that holds the separation column, the end fittings, and the electrospray emitter in place, the plastic material covering a substantial part of the electrospray emitter and extending continuously to cover the one of the end fittings, the separation column, and a substantial part of an additional one of the end fittings, further comprising heating/cooling bars and thermo sensor in contact with the column and embedded in the plastic material.

11. The integrated separation column of claim 1 further comprising counter electrode(s) with a geometry that benefits definition of the field lines around the electrospray emitter.

12. The integrated separation column of claim 11 further comprising channels for gas flow embedded in the same plastic material.

13. An integrated separation column comprising end fittings, a separation column, an electrospray emitter, and a high-voltage contact point for the electrospray emitter, wherein the separation column is connected directly or via a transferring conduit with the electrospray emitter through one of the end fittings, and wherein the separation column, the end fittings, and the electrospray emitter are embedded in a plastic material that forms a housing that holds the separation column, the end fittings, and the electrospray emitter in place, the plastic material covering a substantial part of the electrospray emitter and extending continuously to cover the one of the end fittings, the separation column, and a substantial part of an additional one of the end fittings, wherein the high voltage contact point configured to provide one or more kilovolts, the high-voltage contact point for the electrospray emitter is embedded in the plastic material but penetrates the outer surface of the material to provide an electrical contact for an external power source.

* * * * *

UNITED STATES PATENT AND TRADEMARK OFFICE
CERTIFICATE OF CORRECTION

PATENT NO. : 10,564,137 B2
APPLICATION NO. : 15/052353
DATED : February 18, 2020
INVENTOR(S) : Ole Vorm et al.

Page 1 of 1

It is certified that error appears in the above-identified patent and that said Letters Patent is hereby corrected as shown below:

In the Claims

Claim 12, Column 12, Line 1:
Replace "The integrated separation column of claim 11"
With --The integrated separation column of claim 10--

Signed and Sealed this
Second Day of June, 2020

Andrei Iancu
*Director of the United States Patent and Trademark Office*